United States Patent
Stroop

(10) Patent No.: US 9,486,925 B1
(45) Date of Patent: Nov. 8, 2016

(54) MECHANICAL ARM

(71) Applicant: Jeffrey A. Stroop, Murfreesboro, TN (US)

(72) Inventor: Jeffrey A. Stroop, Murfreesboro, TN (US)

(*) Notice: Subject to any disclaimer, the term of this patent is extended or adjusted under 35 U.S.C. 154(b) by 0 days.

(21) Appl. No.: 15/049,397

(22) Filed: Feb. 22, 2016

(51) Int. Cl.
| | |
|---|---|
| B25J 1/04 | (2006.01) |
| B25J 15/02 | (2006.01) |
| F16H 19/04 | (2006.01) |
| A61F 2/58 | (2006.01) |
| A61F 2/68 | (2006.01) |
| B25J 1/00 | (2006.01) |

(52) U.S. Cl.
CPC ............ B25J 15/0213 (2013.01); A61F 2/586 (2013.01); B25J 1/04 (2013.01); F16H 19/04 (2013.01); A61F 2002/6836 (2013.01); B25J 1/00 (2013.01)

(58) Field of Classification Search
CPC .................................................... B25J 15/0213
See application file for complete search history.

(56) References Cited

U.S. PATENT DOCUMENTS

| | | | | |
|---|---|---|---|---|
| 2,861,701 A * | 11/1958 | Bergsland | ................ | B25J 15/04 279/900 |
| 4,231,603 A | 11/1980 | van Zelm | | |
| 4,441,746 A | 4/1984 | Corboy, Jr. | | |
| 4,547,121 A * | 10/1985 | Nesmith | ................ | B25J 15/103 212/230 |
| 4,573,727 A * | 3/1986 | Iikura | ..................... | B25J 15/02 294/106 |
| 4,613,179 A | 9/1986 | van Zelm | | |
| 4,758,035 A | 7/1988 | Shimasaki | | |
| 5,590,923 A | 1/1997 | Berger et al. | | |
| 7,318,610 B2 | 1/2008 | Nelson et al. | | |
| 8,104,807 B2 * | 1/2012 | Maffeis | ................ | B25J 15/0071 294/119.1 |
| 8,113,557 B2 * | 2/2012 | Kirst | ...................... | B66C 1/447 294/106 |
| 8,235,438 B2 * | 8/2012 | Saadat | ................. | B25J 15/0266 269/32 |
| 9,073,217 B2 * | 7/2015 | Xiao | .................... | B25J 15/0028 |
| 2008/0073922 A1 * | 3/2008 | Holtz | ................... | B25J 15/0213 294/198 |
| 2012/0299322 A1 | 11/2012 | White | | |
| 2013/0088031 A1 * | 4/2013 | Jones | ................... | B25J 15/0028 294/203 |
| 2015/0021948 A1 * | 1/2015 | Xiao | .................... | B25J 15/0028 294/198 |
| 2015/0268258 A1 * | 9/2015 | Jones | ................... | B25J 15/0028 294/202 |

* cited by examiner

*Primary Examiner* — Gerald McClain
(74) *Attorney, Agent, or Firm* — Patterson Intellectual Property Law, P.C.; Mark J. Patterson

(57) ABSTRACT

A mechanical arm includes a frame with a distal end and a proximal end opposite the distal end. At least one gear may be rotatably connected to the frame. The gear may include a series of projections along its circumference. A pair of opposing jaw members may extend beyond the distal end of the frame. At least one jaw member may be connected to a corresponding gear. An elongate member may be slidably disposed on the frame. The elongate member may include a row of teeth configured to operatively mesh with the series of projections of the gear and may cause rotation of the gear upon translation of the elongate member. A handle may be disposed on the frame nearer the distal end than the proximal end. The handle may include an actuator connected to the elongate member. The actuator may translate the elongate member upon actuation.

16 Claims, 5 Drawing Sheets

MECHANICAL ARM

A portion of the invention of this patent document contains material that is subject to copyright protection. The copyright owner has no objection to the reproduction of the patent document or the patent invention, as it appears in the U.S. Patent and Trademark Office patent file or records, but otherwise reserves all copyright rights whatsoever.

CROSS-REFERENCES TO RELATED APPLICATIONS

This application claims benefit of the following patent application(s) which is/are hereby incorporated by reference:
N/A

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to a mechanical arm. More particularly, the present invention pertains to a mechanical arm including at least one gear configured to rotate a respective grip member about an axis.

Mechanical arms of varying types are known in the art. For instance, grabber arms that are children's toys or reaching tools for disabled individuals are available. These types of mechanical arms, however, are not designed to be robust and do not support the wrist of the user.

Robotic arms for industrial purposes such as manufacturing vehicles are also known. While these arms are precise and prevent a user from encountering dangerous environments, they can be prohibitively expensive.

What is needed, therefore, is a mechanical arm that is robust, ergonomic, and providing of at least some protection to a user.

BRIEF SUMMARY OF THE INVENTION

Briefly, the present invention relates, in one embodiment, to a mechanical arm. The mechanical arm may include a frame. The frame may have a gripping end and a receiving end opposite the gripping end. A handle may be disposed on the frame between the gripping end and the receiving end. The handle may include a stationary element connected to the frame and an actuation element translatable relative to the stationary element. The actuation element may be translatable between an actuated position and an unactuated position. At least one elongate member may be connected to the actuation element and extend toward the gripping end. The elongate member may also include a row of gear teeth. First and second opposed grip members may be disposed on the frame. The first grip member may be rotatable about a first axis relative to the frame. At least one first gear may be connected to the first grip member. The first gear may include teeth complementary to the row of gear teeth and may engage the row of gear teeth. The first gear may be configured to rotate the first grip member about the first axis upon translation of the actuation element.

An alternative embodiment of a mechanical arm may further include third and fourth opposed grip members disposed on the frame. The third grip member may be rotatable about the first axis relative to the frame.

Still another embodiment may include a first shaft rotatably mounted to the frame. The first grip member and the at least one first gear may be connected to the first shaft.

Yet another embodiment may include the elongate member further including a second row of gear teeth. The second grip member may be rotatable about a second axis relative to the frame. At least one second gear may be connected to the second grip member. The second gear may include teeth complementary to the second row of gear teeth and may engage the second row of gear teeth. The second gear may be configured to rotate the second grip member about the second axis upon translation of the actuation element.

Another embodiment may include the first axis and second axis oriented parallel to each other.

A further embodiment may include a second shaft rotatably mounted to the frame. The second grip member and the at least one second gear may be connected to the second shaft.

A further still embodiment may include the frame configured to cover at least a portion of a user's hand and forearm during use.

Yet another embodiment may include the frame including at least one support portion configured to at least partially support a user's wrist during use.

Still another embodiment may include at least one resilient member configured to bias the actuating element toward the unactuated position.

An even further embodiment may include the frame further including a gear cover. The gear cover may be configured to at least partially cover the at least one first gear.

Another embodiment may include the frame further including a user cover. The user cover may be configured to cover all portions of a user's hand and arm placed interior to the frame.

One embodiment may include one of a plurality of article engagement elements connected to each of the first and second opposed grip members. The article engagement elements may be configured to engage an article to be manipulated by the mechanical arm.

A further embodiment may include each of the article engagement elements including an elongate finger portion.

A further still embodiment may include each of the article engagement elements including an arcuate portion.

An even further embodiment may include each of the article engagement elements including an engagement surface having at least one protrusion to aid in gripping the article.

Another embodiment may include the article engagement elements removably connected to the first and second opposed grip members to allow for attachment of a variety of different article engagement elements.

The present invention also relates, in one embodiment, to a mechanical arm including a frame having a distal end and a proximal end opposite the distal end. At least one gear may be rotatably connected to the frame. The gear may include a series of projections along a circumference of the gear. A pair of opposing jaw members may extend beyond the distal end of the frame. At least one jaw member may be connected to a corresponding gear of the at least one gear. An elongate member may be slidably disposed on the frame. The elongate member may include a row of teeth configured to operatively mesh with the series of projections of the gear and may cause rotation of the gear upon translation of the elongate member. A handle may be disposed on the frame nearer the distal end than the proximal end. The handle may include an actuator connected to the elongate member. The actuator may be configured to translate the elongate member upon actuation.

In a further embodiment, the frame may have at least one support portion extending from the handle to the proximal end. The support portion may be configured to at least partially support a user's wrist during use.

In another embodiment, a pair of opposing jaw members may be configured to removably receive a variety of interchangeable article engagement elements adapted for varying functions.

The present invention also relates, in an embodiment, to a method of using a mechanical arm. The method may include actuating an actuator disposed on a handle of the mechanical arm; translating a row of teeth; rotating a gear in operative contact with the row of teeth, the gear connected to a corresponding jaw member of a pair of opposing jaw members; and bringing the opposing jaw members closer to each other.

DETAILED DESCRIPTION OF THE INVENTION

Reference will now be made in detail to embodiments of the present invention, one or more drawings of which are set forth herein. Each drawing is provided by way of explanation of the present invention and is not a limitation. In fact, it will be apparent to those skilled in the art that various modifications and variations can be made to the teachings of the present invention without departing from the scope of the invention. For instance, features illustrated or described as part of one embodiment can be used with another embodiment to yield a still further embodiment.

Thus, it is intended that the present invention covers such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only and is not intended as limiting the broader aspects of the present invention.

Figure 1:
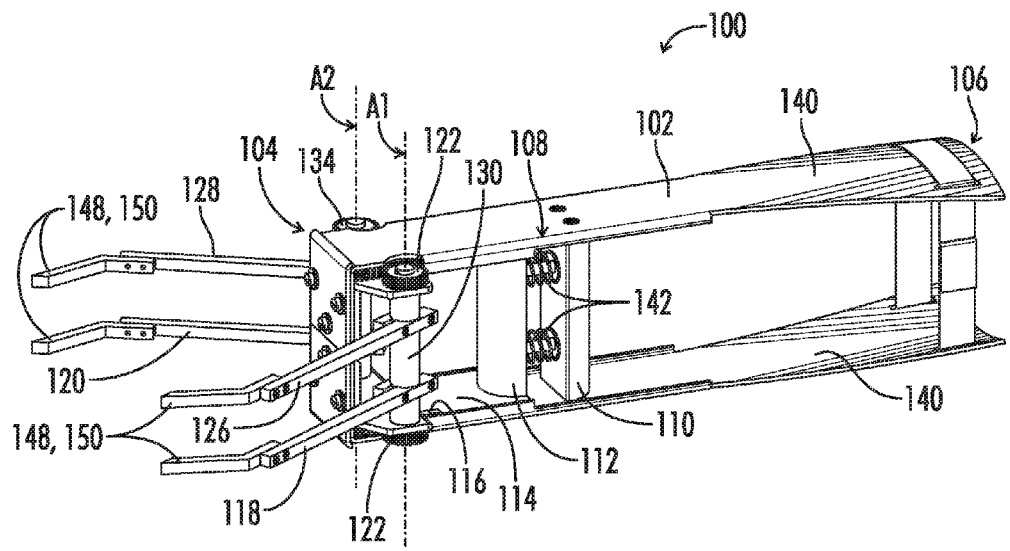
FIG. 1 is a perspective view of one embodiment of the mechanical arm in the open position.

Referring to FIG. 1, a mechanical arm 100 is shown. The mechanical arm 100 may include a frame 102. The frame 102 may be made of any appropriate material including, but not limited to, any sufficiently strong metal, alloy, polymer, polymer mixture, wood, composite, or any combination thereof. The frame 102 may be of any suitable shape including, but not limited to, an elongate flat beam, an elongate beam that curves along the lateral portions, a plurality of connected elongate beams, a prismatic frame with a cross-section perpendicular to the axis that is square (or circular, rectangular, triangular, hexagonal, and the like), a lattice of elongate sections of an appropriate material, one or more pipes of any given cross-sectional geometry (hollow or solid), and the like. The frame 102 may have a gripping end 104 and a receiving end 106 opposite the gripping end. The frame 102 may be of any appropriate geometry. In embodiments forming a passageway interior to the frame 102, the passageway may be of a constant or varying cross-sectional area.

A handle 108 may be disposed on the frame 102 between the gripping end 104 and the receiving end 106. The handle 108 may be of any shape including, but not limited to, a flat beam, a rounded beam, a pistol grip, an arcuate member, any ergonomic shape known in the art, a cantilevered beam, a connected beam, and the like. The handle 108 may include a stationary element 110 connected to the frame 102. The stationary element 110 may be connected to the frame 102 in any manner including, but not limited to, through the use of fasteners such as screws, nuts and bolts, bolts; welding of any kind; gluing; being formed as one part with the frame; and the like. The stationary element 110 may also be connected to the frame 102 in one or more locations.

Figure 2:
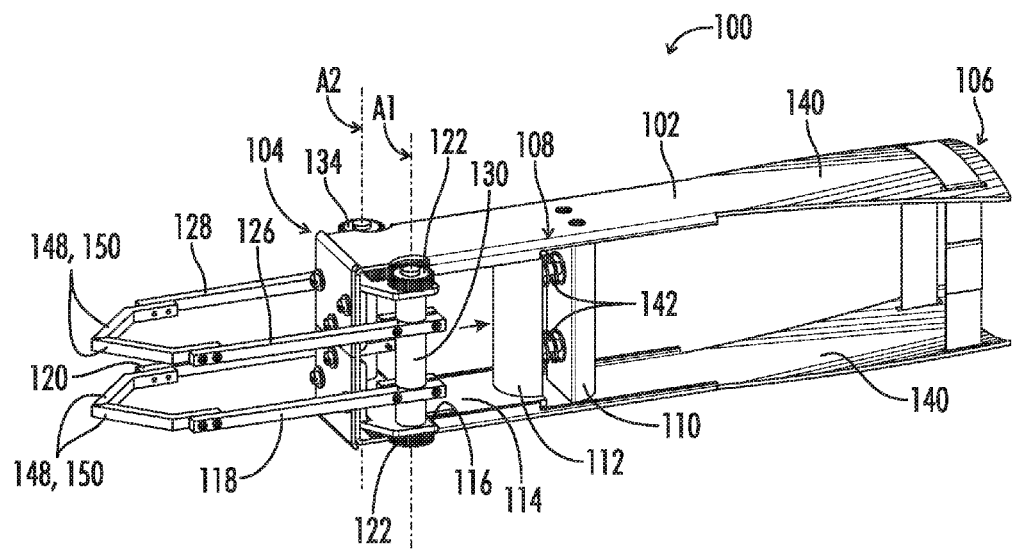
FIG. 2 is a perspective view of the mechanical arm of FIG. 1 in the closed position.

The handle 108 may also include an actuation element 112 translatable relative to the stationary element 110. The actuation element 112 may be translatable between an actuated position (as shown in FIG. 2) and an unactuated position (as shown in FIG. 1). The translation of the actuation element 112 can be any appropriate motion including, but not limited to, linear translatable motion toward and away from the stationary element 110, rotatable motion about an attachment point to the frame 102 or the stationary element, and the like. The actuation element 112 may be translatably attached to the stationary element 110 (along rails, telescoping rods, springs, any combination thereof, and the like), translatably attached to the frame 102, pivotably connected to the frame, pivotably connected to the stationary element, and the like.

At least one elongate member 114 may be connected to the actuation element 112. The elongate member 114 may be attached to the actuation element 112 in any manner including, but not limited to, fastened with any fastener, welded in any way, through the use of adhesives, molded as one part with the actuation element, any combination thereof, and the like. The elongate member 114 may extend from the actuation element 112 toward the gripping end 104 of the frame 102. The elongate member 114 may also include a row of gear teeth 116. The elongate member 114 may be of any appropriate shape and size so as to translate a row of gear teeth. The elongate member 114 may be a plate, a bar, a row of gear teeth thick enough to be attached to the actuation element and maintain its orientation, any combination thereof, and the like.

A first grip member 118 and a second grip member 120 may be disposed on the frame 102. The first grip member 118 and second grip member 120 may oppose each other directly or indirectly including, but not limited to, an orientation anywhere between more than 0 and up to 180 degrees relative to each other. The first grip member 118 may be rotatable about a first axis A1 relative to the frame 102. Any number of grip members may be included in an embodiment of the mechanical arm 100. Each grip member 118, 120 may be of any suitable size and shape. Each grip member 118, 120 may be thicker than what would normally be used in order to be sufficient for industrial applications and the like, or each grip member may be made of stronger or otherwise different material for the same purpose. The grip members 118, 120 may be made of any appropriate material including, but not limited to, metal, alloy, polymer, polymer mixture, wood, composite, or any combination thereof.

At least one first gear 122 may be connected to the first grip member 118. The first gear 122 may be connected to the first grip member 118 in any method of attaching two objects discussed above. The first gear 122 may include teeth 124 complementary to the row of gear teeth 116 and engaging the row of gear teeth. The first gear 122 may also be configured to rotate the first grip member 118 about the first axis A1 upon translation of the actuation element 112. Any number of gears may be used, and each gear may be of any appropriate dimension. The first gear 122, for instance, may be an elongate gear so as to span from one side of the frame 102 to the other side of the frame in one embodiment.

Third grip member 126 and fourth grip member 128 may also be disposed on the frame 102. The third grip member 126 may be rotatable about the first axis A1 relative to the frame 102. The third grip member 126 may move with the first grip member 118, in a different timing than the first grip member, independently of the first grip member, and the like. A first shaft 130 may be rotatably mounted to the frame 102. The first grip member 118 may be connected to the first shaft 130 in any connection manner contemplated above. The first gear 122 may also be connected to the first shaft 130 in any manner.

The elongate member 114 may also include a second row of gear teeth 132 in any configuration as contemplated above with respect to the first row of gear teeth 116. The second grip member 120 may be rotatable about a second axis A2 relative to the frame 102. At least one second gear 134 may be connected to the second grip member 120 in any manner contemplated above with regard to the first gear 122 and first grip member 118. The second gear 134 may include teeth 136 complementary to the second row of gear teeth 132 and engaging the second row of gear teeth. The second gear 134 may be configured to rotate the second grip member 120 about the second axis A2 upon translation of the actuation element 112. In some embodiments, the first axis A1 and the second axis A2 may be parallel or substantially parallel to each other. A second shaft 138 may be rotatably mounted to the frame 102. The second grip member 120 may be connected to the second shaft 138 in any manner of connection contemplated above. The second gear 134 may also be connected to the second shaft 138 in any manner of connection.

In some embodiments, the frame 102 is configured to cover at least a portion of a user's hand and forearm (not shown) during use. The frame 102 may cover one side of a user's hand and forearm that comes into contact with the frame. The frame 102 may include at least one support portion 140 configured to at least partially support a user's wrist (not shown) during use. The support portion 140 may be an integral part of the frame 102 or may be attached to the frame in any manner of attachment as contemplated above. The frame 102 may also include multiple support portions 140 such as 2, 3, 4, or more support portions.

At least one resilient member 142 may be configured to bias the actuation element 112 toward the unactuated position (shown in FIG. 1). The resilient member 142 may be any component or components configured to bias the actuation element 112 toward the unactuated position including, but not limited to, any type of spring, dimensions of the respective parts that biases toward a certain configuration, elastic members, resilient material between the components such as polymers or air bags, and the like. Any number of resilient members 142 may be included, and any combination of resilient members may be used.

The frame 102 may further include a gear cover 144. The gear cover 144 may be configured to at least partially cover the at least one first gear 122. The gear cover 144 may also be configured to cover at least a portion of all the gears 122, 134 of the mechanical arm 100. In one embodiment, the gear cover 144 may substantially cover all the gears 122, 134 and prevent the gears from interacting with any exterior item (such as articles to be manipulated by the mechanical arm 100, a user's finger, foreign contaminants, and the like).

The frame 102 may include a user cover 146. The user cover 146 may be configured to at least partially cover a user's hand and arm (not shown) placed interior to the frame 102. The user cover 146 may also be configured to cover all portions of a user's hand and arm (not shown) placed interior to the frame 102. The user cover 146 may be configured to protect any portion of a user's hand and forearm shrouded by the user cover from unwanted interaction with outside contaminants and forces. The user cover 146 may be any appropriate flexible material that is simply intended to prevent liquid or bacterial contamination of a user's hand and forearm. The user cover 146 may also be any appropriate rigid material to prevent a user's hand from being crushed by articles to be manipulated by the mechanical arm 100 or other objects and machines. The user cover 146 may be a separate part from the frame 102 and attached in any manner contemplated above, integral to the frame, or may be the same portion of the frame as the support portion 140.

At least one of a plurality of article engagement elements 148 is connected to the first grip member 118. At least one of the plurality of article engagement elements 148 is also connected to the second grip member 120. In embodiments including a third grip member 126 and fourth grip member 128, the article engagement elements 148 may also be attached thereto. The grip members 118, 120, 126, 128 may be made of any appropriate material including, but not limited to, metal, alloy, polymer, polymer mixture, wood, composite, or any combination thereof.

Figure 3:
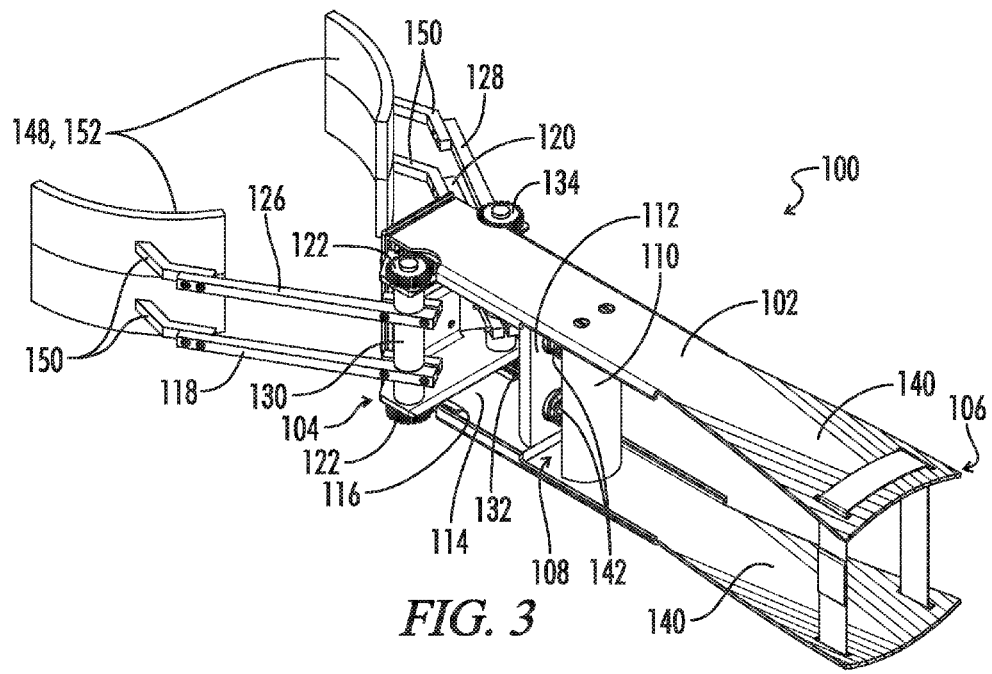
FIG. 3 is a perspective view of the mechanical arm of FIG. 1 with alternative article engagement elements connected thereto.
Figure 4:
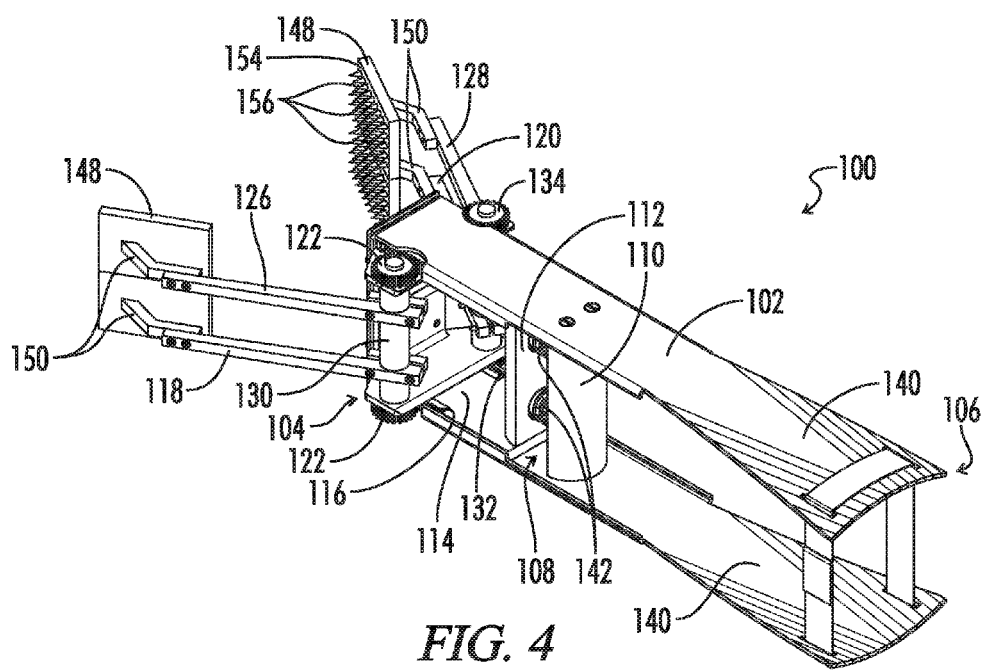
FIG. 4 is a perspective view of the mechanical arm of FIG. 1 with further alternative engagement elements connected thereto.
Figure 5:
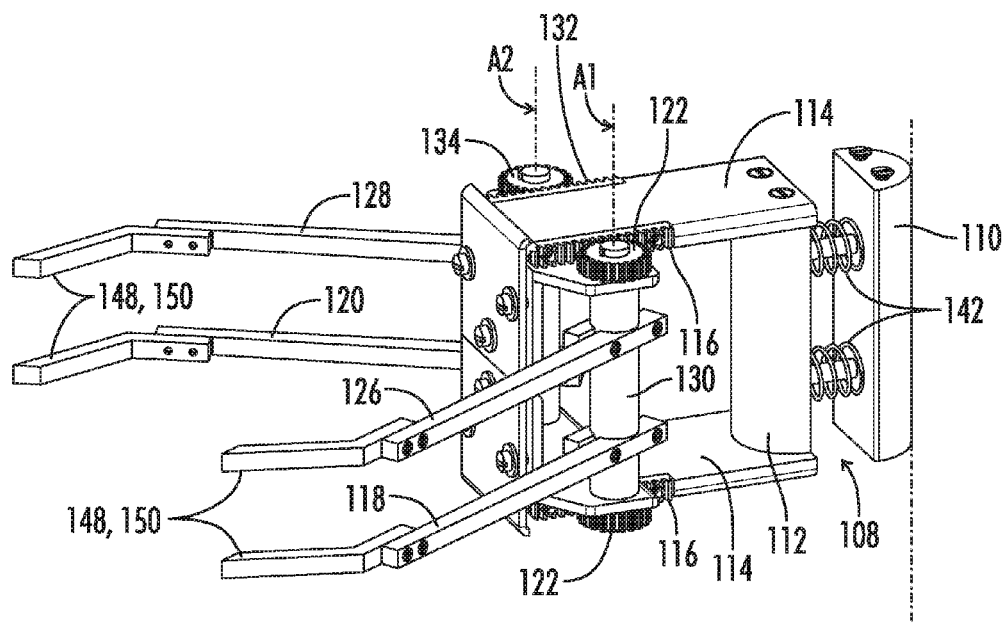
FIG. 5 is a detailed partial perspective view of the mechanical arm of FIG. 1 in the open position without the frame.
Figure 6:
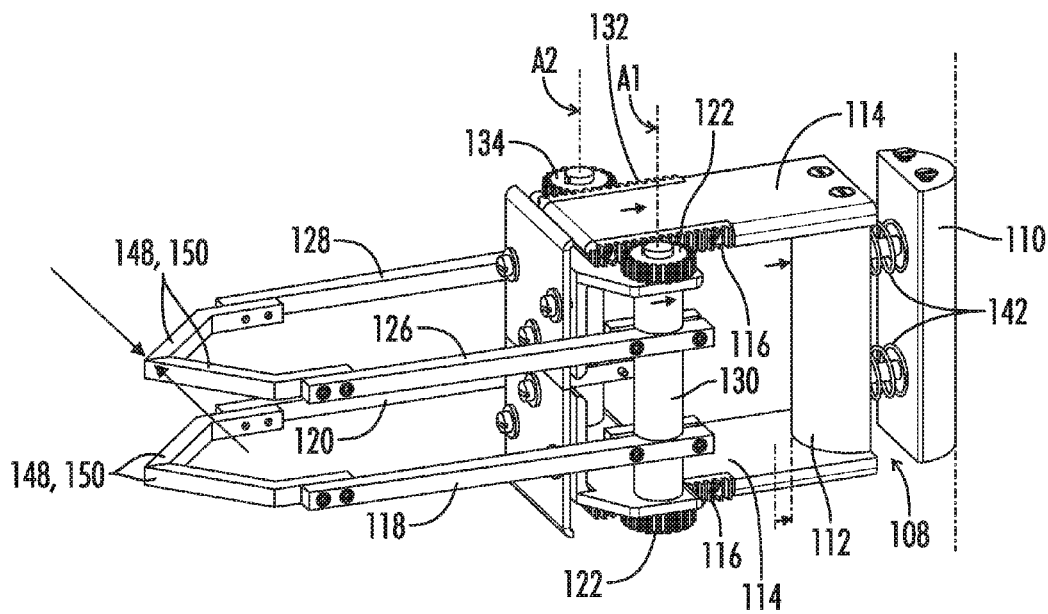
FIG. 6 is a detailed partial perspective view of the mechanical arm of FIG. 1 in the closed position without the frame.
Figure 7:
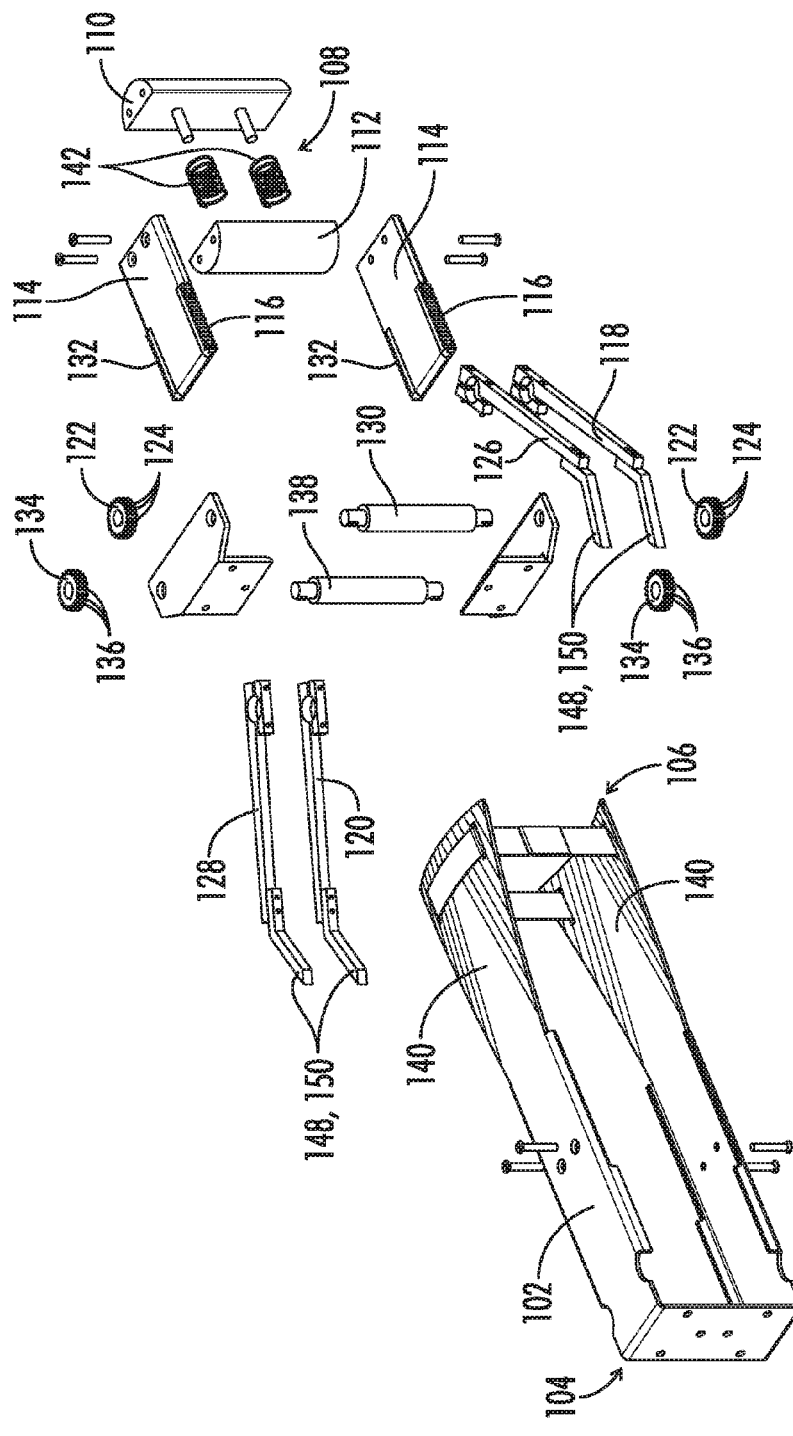
FIG. 7 is an exploded view of the mechanical arm of FIG. 1.
Figure 8:
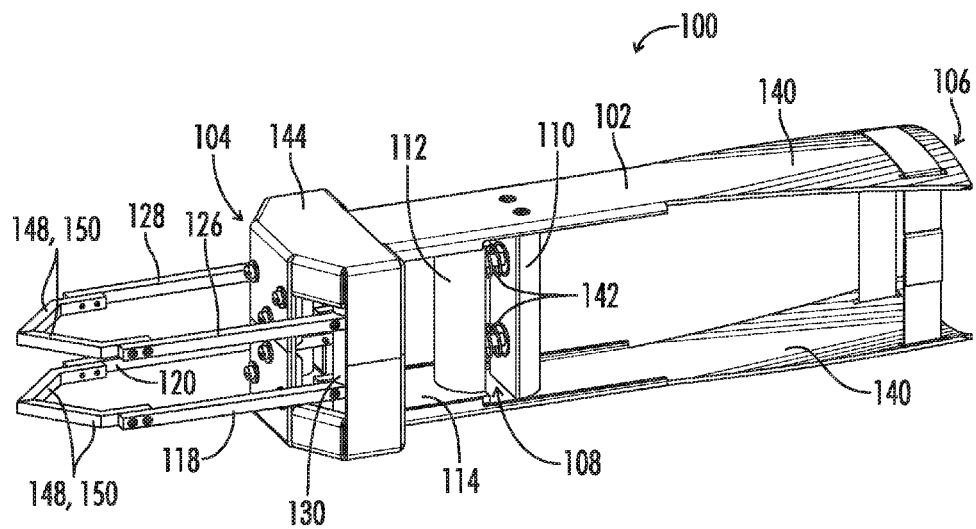
FIG. 8 is a perspective view of the mechanical arm of FIG. 1 including a gear cover.
Figure 9:
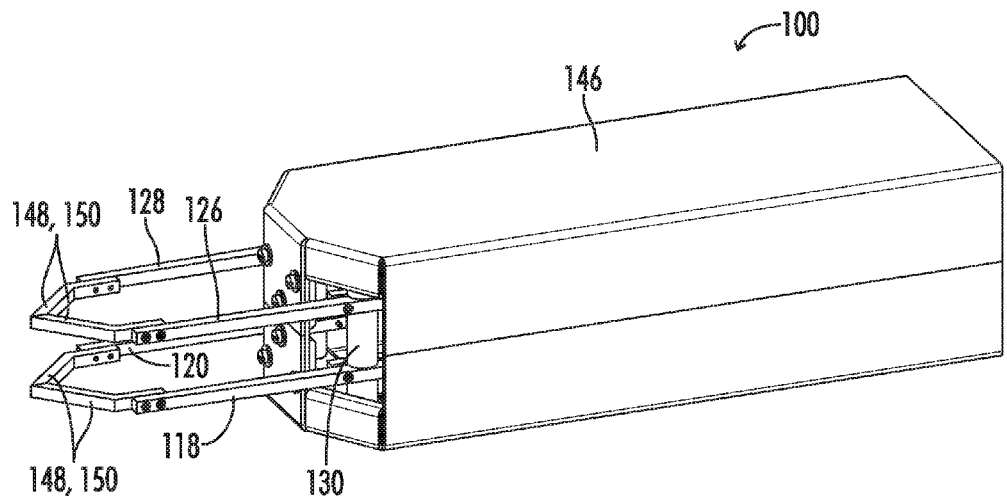
FIG. 9 is a perspective view of the mechanical arm of FIG. 1 including a user cover.

The article engagement elements 148 may be configured to engage an article (not shown) to be manipulated by the mechanical arm 100. In one embodiment, each of the article engagement elements 148 may include an elongate finger portion 150. In another embodiment, each of the article engagement elements 148 may include an arcuate portion 152, as best seen on FIG. 3. As shown in FIG. 4 in still another embodiment, each of the article engagement elements 148 may include an engagement surface 154 having at least one protrusion 156 to aid in gripping an article (not shown). The engagement surface 154 may also include any surface feature that is configured to accomplish a specific function or variety of functions. The engagement surface 154 may include, but is not limited to including, one or more recesses, dimples, bumps, grooves, holes, needles, pins, channels, hooks, and the like. The article engagement elements 148 may include any appropriate attachment to accomplish a specific function or a variety of functions. Some additional article engagement attachments 148 may include, but are not limited to, cutting members, hole punching members, embossing members, piercing members, and the like.

The article engagement elements 148 may be connected to the grip members 118, 120, 126, 128 in any manner contemplated above. In one embodiment, the article engagement elements 148 may be removably connected to the first grip member 118 and the second grip member 120 (and third grip member 126 and fourth grip member 128 in embodiments including them). This removable connection may allow for attachment of a variety of different article engagement elements 148. Any combination of article engagement elements 148 may be used in order to accomplish desired functions with the mechanical arm 100, including mixing and matching varying article engagement elements. The article engagement elements 148 may be made of any suitable material including, but not limited to metal, alloy, polymer, polymer mixture, wood, composite, or any combination thereof. Some article engagement elements 148 may be made of a different material than others to be suitable for different purposes.

This written description uses examples to disclose the invention and also to enable any person skilled in the art to practice the invention, including making and using any devices or systems. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Although embodiments of the invention have been described using specific terms, such description is for illustrative purposes only. The words used are words of description rather than limitation. It is to be understood that changes and variations may be made by those of ordinary skill in the art without departing from the spirit or the scope of the present invention, which is set forth in the following claims. In addition, it should be understood that aspects of the various embodiments may be interchanged in whole or in part. While specific uses for the subject matter of the invention have been exemplified, other uses are contemplated. Therefore, the spirit and scope of the appended claims should not be limited to the description of the versions contained herein.

The invention claimed is:

1. A mechanical arm comprising:
   a frame having a gripping end and a receiving end opposite the gripping end;
   a handle disposed on the frame between the gripping end and the receiving end, the handle comprising:
      a stationary element connected to the frame, and
      an actuation element translatable relative to the stationary element between an actuated position and an unactuated position;
   at least one elongate member connected to the actuation element and extending toward the gripping end, the elongate member including a row of gear teeth;
   first and second opposed grip members disposed on the frame, the first grip member rotatable about a first axis relative to the frame;
   a first gear connected to the first grip member, the first gear including teeth complementary to the row of gear teeth and engaging the row of gear teeth, the first gear configured to rotate the first grip member about the first axis upon translation of the actuation element; and
   wherein the frame and the handle define an uninterrupted lateral opening between the handle and the gripping end of the frame.

2. The mechanical arm of claim 1, further comprising third and fourth opposed grip members disposed on the frame, the third grip member rotatable about the first axis relative to the frame.

3. The mechanical arm of claim 1, further comprising a first shaft rotatably mounted to the frame, the first grip member and the at least one first gear connected to the first shaft.

4. The mechanical arm of claim 1, further comprising:
   the elongate member further including a second row of gear teeth;
   the second grip member rotatable about a second axis relative to the frame; and
   at least one second gear connected to the second grip member, the second gear including teeth complementary to the second row of gear teeth and engaging the second row of gear teeth, the second gear configured to rotate the second grip member about the second axis upon translation of the actuation element.

5. The mechanical arm of claim 4, wherein the first axis and the second axis are parallel.

6. The mechanical arm of claim 4, further comprising a second shaft rotatably mounted to the frame, the second grip member and the at least one second gear connected to the second shaft.

7. The mechanical arm of claim 1, wherein the frame defines a passageway from the receiving end to the handle.

8. The mechanical arm of claim 7, wherein the frame includes at least one support portion defining the passageway.

9. The mechanical arm of claim 1, further comprising at least one resilient member configured to bias the actuation element toward the unactuated position.

10. The mechanical arm of claim 1, further comprising a gear cover disposed on the frame, the gear cover configured to at least partially cover the first gear.

11. The mechanical arm of claim 1, further comprising a user cover disposed on the frame and covering at least a portion of the uninterrupted lateral opening.

12. The mechanical arm of claim 1, further comprising a plurality of article engagement elements connected to each of the first and second opposed grip members, the article engagement elements configured to engage an article to be manipulated by the mechanical arm.

13. The mechanical arm of claim 12, wherein each of the article engagement elements includes an elongate finger portion.

14. The mechanical arm of claim 12, wherein each of the article engagement elements includes an arcuate portion.

15. The mechanical arm of claim 12, wherein each of the article engagement elements includes an engagement surface having at least one protrusion to aid in gripping the article.

16. The mechanical arm of claim 12, wherein the article engagement elements are removably connected to the first and second opposed grip members to allow for attachment of a variety of different article engagement elements.

* * * * *